United States Patent [19]
Garrity et al.

[11] Patent Number: 5,268,281
[45] Date of Patent: Dec. 7, 1993

[54] CYCLIC FR-900520 MICROBIAL BIOTRANSFORMATION AGENT

[75] Inventors: George M. Garrity, Westfield; Magda M. Gagliardi, Somerset; Shieh-Shung T. Chen, Morganville, all of N.J.

[73] Assignee: Merck & Co., Inc., Rahway, N.J.

[21] Appl. No.: 952,102

[22] Filed: Sep. 28, 1992

[51] Int. Cl.$^5$ .................... C12P 17/18; C12P 1/04
[52] U.S. Cl. ........................ 435/119; 435/170
[58] Field of Search ......................... 435/170, 119

[56]  References Cited

U.S. PATENT DOCUMENTS

| 3,244,592 | 4/1966 | Arai | 424/115 |
| 4,081,531 | 3/1978 | Arai | 424/121 |
| 4,242,453 | 12/1980 | Umezawa et al. | 435/123 |
| 4,264,607 | 4/1981 | Dewey et al. | 424/263 |
| 4,894,344 | 1/1990 | Sugiyama et al. | 435/899 |
| 4,894,366 | 1/1990 | Okuhara et al. | 514/63 |
| 5,149,701 | 9/1992 | Shafiee et al. | 514/183 |

FOREIGN PATENT DOCUMENTS

| 0184162 | 6/1986 | European Pat. Off. | 498/18 |
| 0349049 | 1/1990 | European Pat. Off. | 17/18 |
| 0349061 | 1/1990 | European Pat. Off. | 15/4 |
| 0388152 | 9/1990 | European Pat. Off. | 19/26 |
| 0388153 | 9/1990 | European Pat. Off. | 19/1 |
| 89/05304 | 6/1989 | PCT Int'l Appl. | 19/1 |
| 715362 | 9/1954 | United Kingdom . | |
| 1060444 | 3/1967 | United Kingdom . | |

OTHER PUBLICATIONS

Hatanaka et al., The Journal of Antibiotics, XLI (11), 1592-1601, (Nov. 1988).
Hatanaka et al., The Journal of Antibiotics, XLII (4), 620-622, (Apr. 1989).
Arai et al., J. Antibiotics, Ser. A. 15, (1962) pp. 231-232.

Primary Examiner—Douglas W. Robinson
Assistant Examiner—Maria Osoteo
Attorney, Agent, or Firm—Charles M. Caruso; Robert J. North; Carol S. Quagliato

[57]  ABSTRACT

Described is a process for producing a new immunosuppressant, a C-19/C-22 cyclic hemiketal (Compound I) biotransformation analog of FR-900520, under novel fermentation conditions utilizing the novel microorganism, Streptomyces sp. (Merck Culture Collection MA6968) ATCC No. 55279. The macrolide immunosuppressant is useful in preventing human host rejection of foreign organ transplants, e.g. bone marrow, liver, lung, kidney and heart transplants.

4 Claims, 1 Drawing Sheet

CYCLIC FR-900520 MICROBIAL BIOTRANSFORMATION AGENT

BACKGROUND OF THE INVENTION

1. Field of the Invention

This invention relates to a novel process for the production of a new FK-506 type immunosuppressant agent, a C-19/C-23 cyclic hemiketal biotransformation analog of FK-900520 (Compound I), utilizing the novel microorganism Streptomyces sp. (MA6968), ATCC No. 55279. The process involves culturing the microorganism in the presence of FR-900520 under fermentation conditions which effect the biotransformation of FR-900520. Also disclosed is a method of its use in a human host for treatment of autoimmune diseases, infectious diseases and/or prevention of organ transplant rejections.

2. Brief Description of Disclosures in the Art

In 1983, the U.S. FDA approved cyclosporin, and extremely effective anti-rejection drug that revolutionized the field of organ transplant surgery. The drug acts by inhibiting the body's immune system from mobilizing its vast arsenal of natural protecting agents to reject the transplant's foreign protein.

As effective as the drug is in fighting transplantation rejection, it suffers drawbacks in causing kidney failure, liver damage and ulcers which in many cases can be very severe.

EPO Publication No. 0184162 to Fujisawa, describes a new macrolide immunosuppressant FK-506 which is reputed to be 100 times more effective than cyclosporin. The macrolide is produced by fermentation of a particular strain of Streptomyces tsukubaensis. Also described is the closely related macrolide immunosuppressant FR-900520, produced by S. hygroscopicus subsp. yakushimaensis.

U.S. Pat. No. 3,244,592 to T. Arai describes the culturing of Streptomyces hygroscopicus var. ascomyceticus to produce the antifungal "ascomycin", which has been shown to be the same compound as FR-900520.

However, there is no description in the literature of the production of any FK-506 type immunosuppressive agents which substantially lack the side effects or similar side effects of cyclosporin. In this regard, new FK-506 type immunosuppressants are continuously being searched for.

SUMMARY OF THE INVENTION

Figure 1:
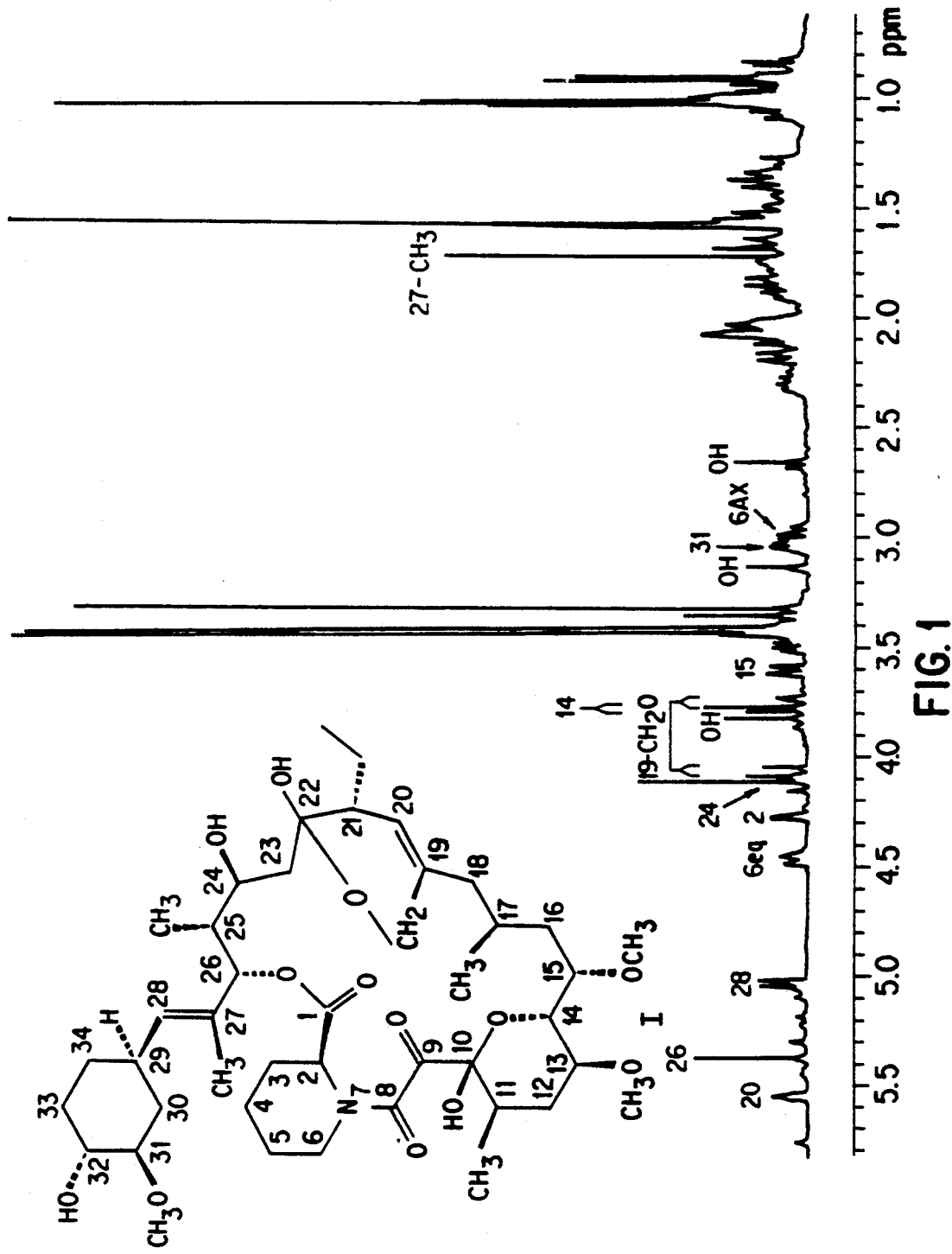
FIG. 1 is an $^1$H nuclear magnetic resonance (NMR) spectrum taken at 400 MHz of Compound I in CDCl$_3$, and also illustrates the assigned molecular structure of the compound.

It has been found that a new FK-506 type immunosuppressant, Compound I, can be obtained by the fermentation of the microorganism Streptomyces sp. (MA6968), ATCC No. 55279, together with the macrolide immunosuppressant FR-900520, under submerged aerobic conditions in an aqueous carbohydrate medium, containing a nitrogen nutrient, said conditions being conducted at a pH of about 7, for a sufficient time to biotransform FR-900520 and produce Compound I. Compound I exhibits a proton nuclear magnetic resonance spectrum illustrated in FIG. 1, and has an assigned structural formula as also identified in FIG. 1.

The resultant Compound I exhibits FK-506 immunosuppressant activity, i.e., positive inhibition of T-cell activation, as demonstrated by the calcium ionophore (ionomycin) plus phorbol myristate acetate (PMA) induced T-cell stimulation assay, also referred to herein as the "T-cell proliferation assay".

The principle of this assay is to measure the proliferation of mouse T lymphocytes stimulated with the combination of ionomycin plus PMA. A positive sample, e.g. FK-506, in this assay will inhibit T-cell proliferation, as indicated by reduced tritiated thymidine uptake.

In addition, there is provided a method of use for treating human host to prevent transplantation rejection, or for treating autoimmune disease or infectious disease comprising administering to said host a therapeutically effective amount of Compound I.

Furthermore there is provided a substantially pure culture of Streptomyces sp., (MA6968), ATCC No. 55279.

DETAILED DESCRIPTION OF THE INVENTION

The present invention involves the fermentation of Streptomyces sp., MA6968, ATCC No. 55279, together with FR-900520 (also known as FK-520) to produce Compound I.

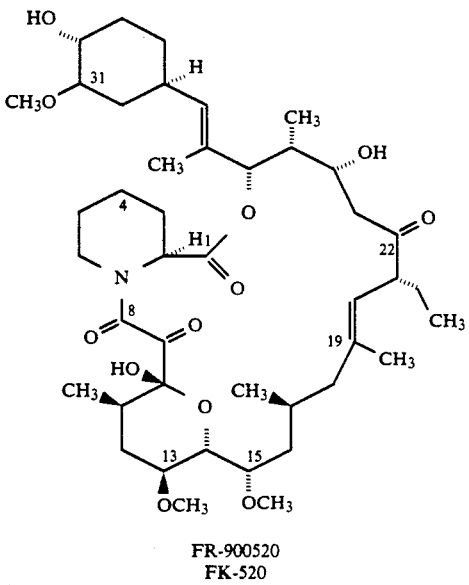

FR-900520
FK-520

A biologically pure sample of the microorganism used in the instant process is currently on deposit with the American Type Culture Collection, 12301 Parklawn Drive in Rockville, Md. as ATCC No. 55279, and in the Merck Culture Collection in Rahway, N.J. as MA6968.

The physical characteristics and taxonomy, including morphological, cultural, biological and physiological characteristics of Streptomyces sp. strain MA6968, ATTC No. 55279 are briefly described hereinbelow. Observations of growth, general cultural characteristics and carbon source utilization were made in accordance with the methods of Shirling and Gottleib (Internat. J. System. Bacteriol. 16: 313-340). Chemical composition of the cells was determined using the methods of Lechevalier and Lechevalier (in Actinomycete Taxonomy, A. Dietz and D. W. Thayer, Ed. Society for Industrial Microbiology, 1980). Coloration of the culture was determined by comparison with color standards contained in the Inter-Society Color Council-National Bureau of Standards Centroid Color Charts (U.S. Dept. of Commerce National Bureau of Standards supplement to NBS Circular 553, 1985).

Source-This culture was isolated from a sample of compost collected in Sommerset, N.J.

Analysis of Cell Wall Composition-Petidoglycan contains LL-diaminopimelic acid.

General growth characteristics-Good growth on yeast malt extract agar (YME), glucose asparagine agar, inorganic salt starch agar, oatmeal agar, trypticase soy agar and peptone iron agar. Poor growth on Czapek's agar and tap water agar supplemented with NZ-amine (Shefield Chemical Co.). Culture also grows in tryptone yeast extract broth. Culture grows at 27° C. and 37° C.

Colony morphology-(on YME at 21 d) Substrate mycelium is dark brown. Aerial mycelium is white. Spore mass is abundant and yellowish white in color. Colonies are opaque, raised and have entire edges, rubbery in texture and have a matte surface.

Micromorphology-Aerial mycelia (0.57–0.72 μm) arise from substrate mycelia and are branched, and flexous. In mature cultures (7–28d p.i.) the aerial mycelium terminates in chains of spores that are slightly flexous (rectus flexibilis). Sporulation occurs on YME, inorganic salts-starch agar, oatmeal, glycerol asparagine agar, Czapek's agar.

Miscellaneous physiological reactions-Culture produces $H_2S$ in peptone-iron agar. Melanoid pigments are formed in peptone iron agar and trypton-yeast extract broth. Starch is not hydrolyzed. A brown diffusible pigment is produced on YME, oatmeal and glucose-asparagine agar. Carbon source utilization pattern is as follows: moderate utilization of α-D-glucose, D-maltose and D-mannose; poor or no utilization of D-arabinose, L-arabinose, D-fructose, inositol, α-D-lactose, β-D-lactose; D-mannitol, D-mannose, D-raffinose, L-rhamnose, sucrose, D-xylose.

Diagnosis-Cell wall analysis reveals that MA6968 has a type I cell wall. Morphological studies reveal that the culture produces flexous chains of spores that arise from the aerial mycelium. These are characteristics typical for strains of Streptomyces. A comparison of the phenotypic data of MA6968 with that of the validly published species of Streptomyces in the taxonomic literature (1–8) failed to reveal any that bore resemblance. Based upon these findings, MA6968 is believed to be a representative isolated of previously undescribed species of Streptomyces, Confirmation of this finding will require additional genetic and chemotaxonomic studies. Therefore, the strain should be referred to a Streptomyces, sp.

Bibliography

1. Shirling, E. B. and Gottlieb, D., Int. J. System. Bacteriol. 18: 69 (1968)
2. Shirling, E. B. and Gottlieb, D., Int. J. System. Bacteriol. 18: 279 (1968)
3. Shirling, E. B. and Gottlieb, D., Int. J. System. Bacteriol. 19: 391 (1969)
4. Shirling, E. B. and Gottlieb, D., Int. J. System. Bacteriol. 22: 265 (1972)
5. Nonomura, H. J. Ferment. Technol. 52: 78 (1974)
6. Pridham, T. and Tresner, H., in Bergey's Manual of Determinative Bacteriology, Eighth Edition, R. E. Buchanan and N. E. Gibbons, Ed., Williams and Wilkins, Baltimore (1974)
7. Loci, R. in Bergey's Manual of Systematic Bacteriology, Vol 4., St. Williams, M. E. Sharpe and J. G. Holt. Ed., Williams and Wilkins, Baltimore (1989)

| Carbohydrate utilization pattern of Streptomyces sp. MA6968 at 21 days | |
|---|---|
| Carbon source | Utilization |
| D-arabinose | 0 |
| L-arabinose | 0 |
| D-fructose | 0 |
| inositol | 1 |
| α-D-lactose | 0 |
| β-D-lactose | 0 |
| D-maltose | 2 |
| D-mannitol | 0 |
| D-mannose | 2 |
| D-raffinose | 0 |
| L-rhamnose | 0 |
| sucrose | 0 |
| D-xylose | 1 |
| α-D-glucose (control) | 2 |

3 = good utilization
2 = moderate utilization
1 = poor utilization
0 = no utilization

| Cultural characteristics of Streptomyces sp MA6968 at 21 days | | | | |
|---|---|---|---|---|
| Medium | Amount of Growth | Aerial Mycelium and or Spores | Soluble Pigments | Reverse Color |
| Yeast Extract Malt Extract | good | Aerial mycelium yellow white (92 y. White). Spores borne in slighty flexous chains. | brown | Dark brown (59 D. Br) |
| Glucose Asparagine | good | Aerial mycelium yellow white (92 y. White). Spores borne in slightly flexous chains. | brown | Slight yellow brown (58 M. Br) |
| Inorganic Salts Starch | good | Aerial mycelium yellow (93 yellow). Spores borne in slightly flexous chains. | none notes | Light yellowish brown (74 s. y Br) |
| Oatmeal | good | Aerial mycelium yellow white (92 y. White). Spores borne in slightly flexous chains. | brown | Slight brown (55 s. Br) |
| Tap Water | sparse | No aerial mass observed | none noted | Transparent |
| Czpak | sparse | No aerial mass observed | none noted | Transparent |
| Peptone Iron | good | | Melanin positive, $H_2S$ | |

| Medium | Cultural characteristics of Streptomyces sp MA6968 at 21 days | | | |
|---|---|---|---|---|
| | Amount of Growth | Aerial Mycelium and or Spores | Soluble Pigments | Reverse Color |
| | | | positive. | |

The present invention process can be practiced with any Compound I producing strain of Streptomyces sp., and particularly preferred is the ATCC No. 55279 strain (MA6968).

In general, Compound I can be produced by culturing the MA6869 strain in the presence of an appropriate concentration of substrate compound FR-900520 in an aqueous nutrient medium containing sources of assimilable carbon and nitrogen, preferably under submerged aerobic conditions (e.g. shaking culture, submerged culture, etc.). An appropriate concentration of substrate compound FR-900520 in the aqueous medium ranges from 0.05 mg/ml to 0.3 mg/ml, and preferably 0.1 mg/ml; less than 0.05 mg/ml is inefficient and greater than 0.3 mg/ml can inhibit the culture. The aqueous medium is preferably maintained at a pH of about 7 at the initiation and termination (harvest) of the fermentation process. A higher pH leads to substantial and/or total loss of product. The desired pH may be maintained by the use of a buffer such as morpholinoethanesulfonic acid (MES), morpholinopropanesulfonic acid (MOPS), and the like, or by choice of nutrient materials which inherently possess buffering properties, such as production media described hereinbelow.

The preferred sources of carbon in the nutrient medium are carbohydrates such as glucose, xylose, galactose, glycerin, starch, dextrin, and the like. Other sources which may be included are maltose, raffinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, polypropylene glycol, mineral oil or silicone may be added.

The FR-900520 starting material (also referred to in the art as "FK-520") can be obtained by the fermentation of S. hygroscopicus var. ascomyceticus, ATCC No. 14891, as described in U.S. Pat. No. 3,244,592, and by the fermentation of S. hygroscopicus subsp. yakushimaensis No. 7278, to produce FR-900520, as described in EPO Publication No. 0184162 to Fujisawa, and U.S. Pat. No. 4,894,366.

Submerged aerobic cultural conditions are preferred for the production of Compound I in massive amounts. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of Compound I.

Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is substantially the same as or different from the medium utilized for the production of Compound I and is generally autoclaved to sterilize the medium prior to inoculation. The pH of the medium is generally adjusted to about 7.0 prior to the autoclaving step by suitable addition of an acid or base, preferably in the form of a buffering solution. The temperature of the seed medium is maintained between 25° C. and 29° C., preferably 27° C.; culture growth will be inhibited below this range and culture death can occur above this range. Incubation of the seed medium is usually conducted for a period of about 15 to 24 hours, preferably 24 hours, on a rotary shaker operating at 220 rpm with a throw of about 2 inches; the length of incubation may be varied according to fermentation condition and scales.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixtue.

The fermentation is usually conducted at a temperature between about 25° C. and 37° C., preferably 25°-30° C., for a period of about 48 hours to 60 hours, which may be varied according to fermentation conditions and scales. Preferably, the production cultures are incubated for about 48 hours at 27° C. on a rotary shaker operating at about 220 rpm with a throw of about 2 inches, wherein the pH of the fermentation medium is maintained at 7.0 to harvest.

Preferred culturing/production media for carrying out the fermentation include the following media:

| | g/liter |
|---|---|
| Seed Medium | |
| Dextrose | 1.0 |
| Dextrin | 10.0 |
| Beef Extract | 3.0 |
| Ardamine pH | 5.0 |
| NZ Amine Type E | 5.0 |
| $MgSO_4 \cdot 7H_2O$ | 0.05 |
| $K_2HPO_4$ | 0.37 |
| Adjust pH to 7.1 | |

-continued

| | g/liter |
|---|---|
| Add CaCO₃ 0.5 g/l | |
| Transformation Medium B | |
| Glucose | 20 |
| Soya Meal | 5 |
| Yeast Autolysate | 5 |
| NaCl | 5 |
| MES | 9.8 |
| Adjust pH to 7.0 | |

The produced Compound I can be recovered from the culture medium by conventional means which are commonly used for the recovery of other known biologically active substances. The Compound I substance produced is found in the cultured mycelium and filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methanol and the like, pH adjustment, treatment with a conventional resin (e.g. anion or cation exchange resin, non-ionic adsorption resin, etc.). treatment with a conventional adsorbent (e.g. activated charcoal, silicic acid, silica gel, cellulose, alumina, etc.), crystallization, recrystallization, chromatography, and the like. A preferred recovery method is solvent extraction, particularly using $CH_2Cl_2$. A preferred purification method involves the use of chromatography, especially HPLC, using a reversed phase silica gel column and an eluant mixture composed of water and an organic solvent such as methanol, acetonitrile and the like, and a small amount of acid such as, e.g., phosphoric acid, acetic acid, trifluoroacetic acid and the like. A preferred eluant is composed of water, acetonitrile, and 0.1% phosphoric acid, and is run through the column in a linear gradient.

The product Compound I from the fermentation exhibits positive immunosuppressive activity by the "T-cell proliferation assay" and posseses utility on this basis and exhibits the following physical characteristics:
1. White amorphous powder
2. Solubility in methanol
3. Molecular weight of 807, as determined by FAB mass spectroscopy which is consistent with the assigned structure in FIG. 1.

It is to be noted that in the aforementioned fermentation reactions and the post-treatment of the fermentation mixture therein, the conformer and/or stereo isomer(s) of Compound I due to asymmetric carbon atom(s) or double bond(s) of Compound I may occasionally be transformed into the other conformer and/or stereoisomer(s), and such cases are also included within the scope of the present invention. It should be noted that Compound I may also occur in its C-19-hydroxymethyl/C-22-keto ring-opened form, and such cases are also included within the scope of the present invention.

Compound I of the present invention possesses immunosuppressant pharmacological activity and therefore is useful in a therapeutic program involving FK-506 type therapy designed for the treatment and prevention of the transplantation rejection of organs or tissues such as heart, kidney, liver, medulla ossium, skin, etc., graft-versus-host diseases by medulla ossium transplantation, autoimmune diseases such as rheumatoid arthritis, systemic lupus erythematosus, Hashimoto's thyroiditis, multiple sclerosis, myasthenia gravis, type I diabetes, uveitis, and the like.

The pharmaceutical composition of this invention can be used in the form of a pharmaceutical preparation, for example, in solid, semisolid or liquid form, which contains Compound I, of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of diseases.

For applying this composition to a human it is preferable to apply it by parenteral or enteral administration. While the therapeutically effective dosage of Compound I will vary from patient to patient, depending upon a variety of factors recognized by those skilled in the art, such as the age, condition and weight of the patient, a daily dose (calculated on the basis of a 70 kg man) of about 0.01-1000 mg, preferably 0.1-500 mg and more preferably 0.5-100 mg, of the active ingredient is generally given for treating diseases, and an average single dose of about 0.5 mg, 1 mg, 5 mg, 10 mg, 50 mg, 100 mg, 250 mg and 500 mg is generally administered.

The following examples are given for the purpose of illustrating the present invention and should not be construed as being limitations on the scope or spirit of the instant invention.

EXAMPLE 1

Microorganism and Culture Conditions

A frozen vial (2.0 ml) of culture MA6968, ATCC No. 55279, was used to inoculate a 250 ml baffled shake flask containing 50 ml of an autoclaved (sterilized) seed medium consisting of (in units of grams/liter) dextrin 10.0, dextrose 1.0, beef extract 3.0, ardamine PH (Yeast Products, Inc.) 5.0, N-Z Amine type E 5.0, $MgSO_4.7H_2O$ 0.05, $KH_2PO_4$ 0.3, and $CaCO_3$ 0.5. The pH of the seed medium was adjusted to 7.1 before autoclaving. The seed was incubated in the seed medium at 27° C. for 24 hours on a rotary shaker operating at 220 rpm. A 2.5 ml aliquot of the resulting seed medium was used to inoculate a 250 ml non-baffled shake flask containing 50 ml of the following previously autoclaved (sterilized) fermentation medium:

| Soy-Glucose Medium | |
|---|---|
| Glucose | 20.0 |
| Soya Meal | 5.0 |
| Yeast Autolysate | 5.0 |
| NaCl | 5.0 |
| MES | 9.8 |
| Adjust pH to 7.0 | |

FR-900520 (also known as FK-520) was added as a solution in dimethylsulfoxide to the fermentation at zero hour to achieve a final concentration of 0.05 mg/ml concentration. The shake flask contents were subsequently incubated for 48 hrs. at 27° C. on a rotary shaker operating at 220 rpm. This procedure was followed two times and the two resultant broths were combined for isolation and purification.

Isolation and Purification:

The whole broth (100 ml) was extracted three times with methylene chloride (3×50 ml). Methylene chloride extracts were combined, dried over sodium sulfate, and concentrated under vacuum to an oily residue. The residue was dissolved in methanol and subjected to high performance liquid chromatography (HPLC). HPLC was carried out on Whatman Magnum 20 Partisil 10 ODS-3 Column (22.1 mm ID×25 cm) at room temperature and monitored at 205 nm. The column was developed at 7 ml/min over 65 minutes using a linear gradient from 35% to 80% acetonitrile in 0.1% phosphoric acid. The fraction with a retention time of 57 minutes (Compound I) was pooled, adjusted to pH 4.0, evaporated to remove acetonitrile, and desalted using a C18 Sep Pak (Waters Associate) by elution with methanol to yield 0.7 mg of Compound I after evaporation to dryness.

ANALYTICAL SPECTRAL DATA

Mass spectral data of the subject Compound I biotransformation product obtained by the incubation of FR-900520 with culture MA6968, coupled with the proton NMR data, as shown in the spectrum of FIG. 1, is consistent with the following assigned molecular structure (Compound I), which is also shown in FIG. 1:

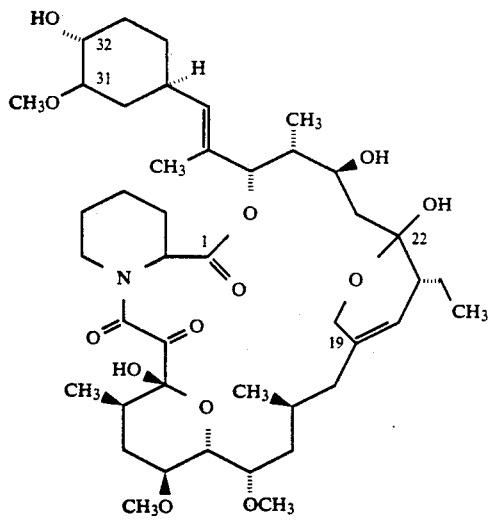

EXAMPLE 2

T-Cell Proliferation Assay

1. Sample Preparation

Purified Compound I, as prepared by HPLC above, was dissolved in absolute ethanol at 1 mg/ml.

2. Assay

Spleens from C57Bl/6 mice were taken under sterile conditions and gently dissociated in ice-cold RPMI 1640 culture medium (GIBCO, Grand Island, N.Y.) supplemented with 10% heat-inactivated fetal calf serum (GIBCO). Cells were pelleted by centrifugation at 1500 rpm for 8 minutes. Contaminating red cells were removed by treating the pellet with ammonium chloride lysing buffer (GIBCO) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 250° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5 \times 10^5$ cells/ml in complete culture medium composed of RPMI 1640 medium with 10% heat-inactivated fetal calf serum, 100 mM glutamine, 1 mM sodium pyruvate, $2 \times 10^{-5}$ M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 200 μl/well. The control, being the medium without test drug, and various below-indicated dilutions of the sample (above-described purified Compound I) to be tested were then added in triplicate wells at 20 μl/well. FR-900506 was used as a standard. The culture plates were then incubated at 37° C. in a humidified atmosphere of 5% $CO_2$-95% air for 44 hours. The proliferation of T lymphocytes was assessed by measurement of tritiated thymidine incorporation. After 44 hours of culturing, the cells were pulse-labelled with 2 μCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Betacounter). Mean counts per minute of replicate wells were calculated and the results expressed as percent inhibition of tritiated thymidine uptake (proliferation) as follows:

$$\% \text{ Inhibition} = \left(100 - \left[\frac{\text{Mean cpm sample tested}}{\text{Mean cpm control medium}}\right]\right) \times 100.$$

The results of % inhibition at various concentrations of Compound I are presented in the following Table:

TABLE

Effects of Compound I on the proliferative response of Splenic T-cells stimulated with ionomycin + PMA

| Sample Concentration of Compound I (nM) | Percent of Inhibition |
|---|---|
| 50.0 | 94 |
| 25.0 | 94 |
| 12.5 | 91 |
| 6.2 | 78 |
| 3.1 | 55 |
| 1.6 | 19 |

TABLE-continued

Effects of Compound I on the proliferative response of Splenic T-cells stimulated with ionomycin + PMA

| Sample | Concentration of Compound I (nM) | Percent of Inhibition |
| --- | --- | --- |
| | 0.8 | 16 |

Notes:

1. Mouse T cell cultures were pulsed with $^3$H-thymidine for 4 hours prior to harvesting at 48 hours.

2. Standard FR-900506 (10 ng/ml) gave 99% inhibition.

3. $IC_{50}$ = 3.17 ng/ml = 3.9 nM, for Compound I, and generally in the range of 1.57 to 5.20 × $10^{-9}$ molar. This is based on a series of 5 additional experiments giving $IC_{50}$ (ng/ml) values of 1.57, 1.92, 5.20, 4.80, 4.50. The mean $IC_{50}$ for all of 6 above runs is 3.52 ± 1.4 (SEM) and 4.36 ± 1.7 nM.

4. Inhibition of T-Cell proliferation by Compound I was reversed by the addition of 50 units/ml of IL-2 (recombinant IL-2) at the initiation of culture.

What is claimed is:

1. A process for the production of an immunosuppressant compound having the structural formula I;

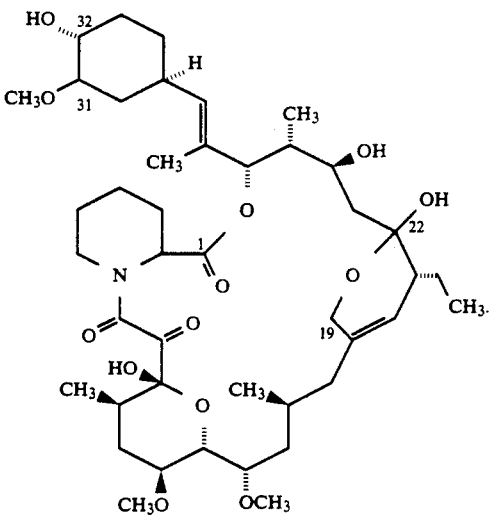

the process comprising the steps of
 (a) culturing a microorganism Streptomyces sp. MA 6968, ATCC No. 55279, in the presence of FR-900520 in an aqueous nutrient medium containing assimilable sources of carbon and nitrogen under aerobic conditions until the compound is produced, and
 (b) recovering the compound.

2. The process of claim 1 wherein the culturing step is conducted for a period of about 48 to 60 hours.

3. The process of claim 1 wherein the culturing step is conducted at a temperature from 25° C. to 37° C.

4. The process of claim 1 wherein the culturing step is conducted at a pH of 7.0.

* * * * *